(12) United States Patent
Menne et al.

(10) Patent No.: US 6,203,521 B1
(45) Date of Patent: Mar. 20, 2001

(54) EJECTION DEVICE FOR THE HIGH-PRESSURE EJECTION OF A LIQUID

(75) Inventors: Andreas Menne; Wolfgang Merkle, both of Meersburg (DE)

(73) Assignee: Ferton Holding SA, Delemont (CH)

( * ) Notice: Subject to any disclaimer, the term of this patent is extended or adjusted under 35 U.S.C. 154(b) by 0 days.

(21) Appl. No.: 09/467,922

(22) Filed: Dec. 21, 1999

(51) Int. Cl.$^7$ ...................................................... A61M 5/30
(52) U.S. Cl. ................. 604/68; 604/70; 604/140
(58) Field of Search ............................... 604/68, 70, 71, 604/140, 141, 143

(56) References Cited

U.S. PATENT DOCUMENTS

| | | | |
|---|---|---|---|
| 5,520,639 | * | 5/1996 | Peterson et al. ...................... 604/68 |
| 5,599,302 | * | 2/1997 | Lilley et al. ........................... 604/68 |
| 5,730,723 | * | 3/1998 | Castellano et al. ................. 604/70 X |
| 5,891,086 | * | 4/1999 | Weston ................................. 604/70 |

* cited by examiner

Primary Examiner—John D. Yasko
(74) Attorney, Agent, or Firm—Griffin & Szipl, P.C.

(57) ABSTRACT

An ejection device 1 for the high-pressure ejection of a liquid or a liquid containing solid particles, comprising a pressure chamber 13 to accommodate the liquid therein, which opens into an ejection opening 11 and is delimited by a working piston 5. The working piston 5 is, upon application of an elastic impact on its end facing away from the pressure chamber 13, capable of transmitting a compression wave which may displace the pressure chamber-facing end of the working piston 5 by a predetermined displacement stroke into the pressure chamber 13 so that the volume thereof is reduced. The reduction in volume of the pressure chamber 13 is signicantly smaller than the volume of the pressure chamber 13. The ejection device 1 further comprises a drive member 24 capable of generating the elastic impact, and is designed such that the working piston 5 is progressively displaced into the pressure chamber 13 by the repeated application of elastic impacts, with the distance of each single displacement being defined by the predetermined displacement stroke. (FIG. 1)

22 Claims, 9 Drawing Sheets

EJECTION DEVICE FOR THE HIGH-PRESSURE EJECTION OF A LIQUID

Figure 1:
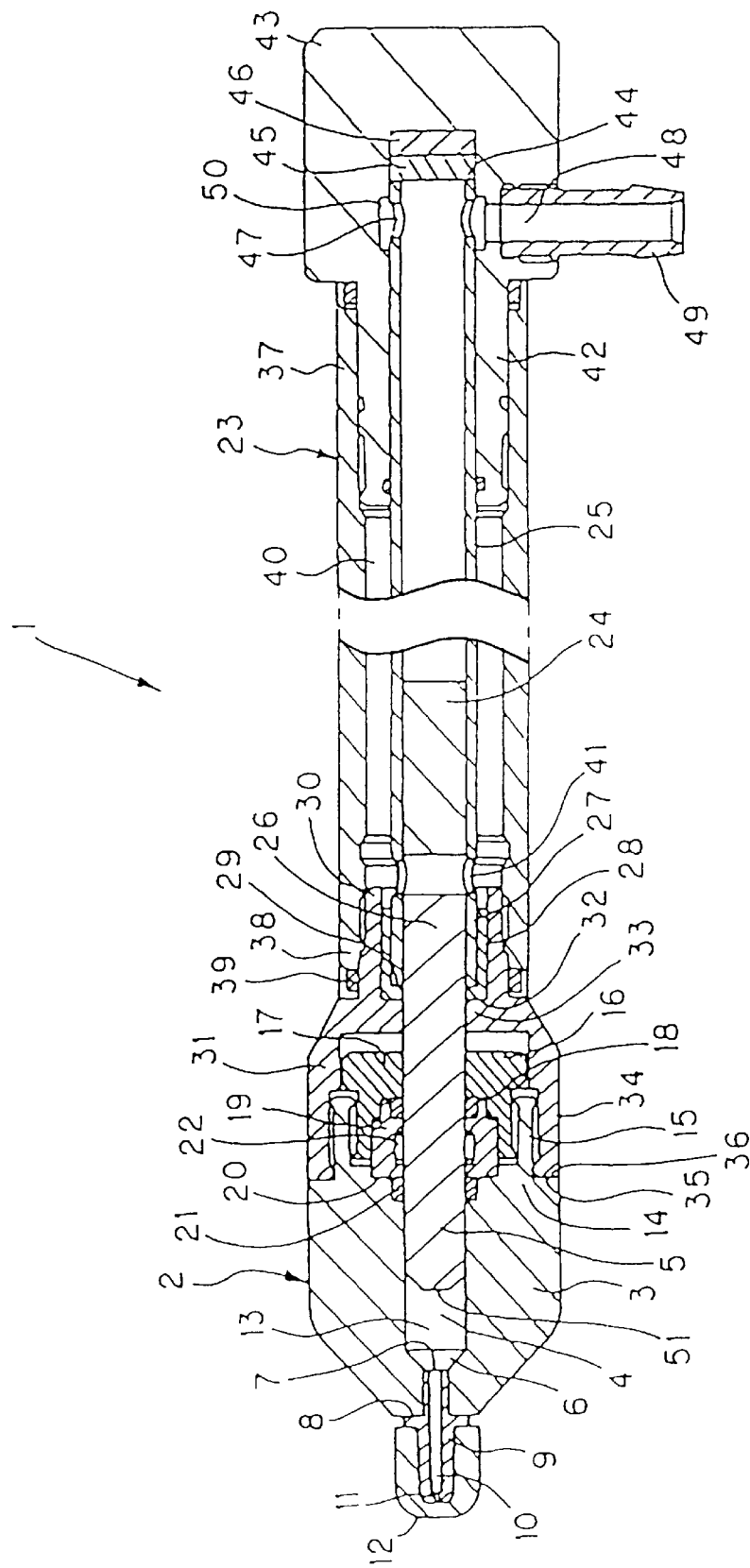

This application claims priority of German Patent Application Number 198 59 135.7-35, filed Dec. 21, 1998, the entire disclosure of which is considered to be part of the present disclosure and is specifically incorporated by reference herein.

The present invention relates to an ejection device for the high-pressure ejection of a liquid or a liquid containing solid particles, comprising a pressure chamber wherein the liquid is received and which opens into an ejection opening and is delimited by a working piston which, upon application of a preferably elastic impact on its end facing away from the pressure chamber, is capable of transmitting a compression wave which may displace the pressure chamber-facing end of the working piston by a predetermined displacement stroke into the pressure chamber so that the volume thereof is reduced. The reduction in volume of the pressure chamber is significantly smaller than the volume of the pressure chamber. Further, the ejection device comprises a drive member which is capable of generating the elastic impact.

An ejection device of the above described type is known, for example, from EP 0 771 219, which describes said device as being specially designed for the ejection of precisely dosed, minute amounts of liquid, which may be in the range of cubic millimeters, so that it is particularly well-suited as a medical instrument for the injecton of minute doses of liquid drugs which are to be administered with high precision.

The ejection of such small amounts of liquid is achieved by the drive member transmitting only an elastic impact to the working piston so that the latter is not moved any further into the pressure chamber. That is, after having transmitted the impact, the drive member no longer exerts any external driving force upon the working piston so that the amount of liquid contained in the pressure chamber and defined by the working piston is not ejected in the way it would in a common syringe, but exclusively by means of the compression wave which is excited by the impact transmitted through the working piston. The working piston transmits a high-pressure pulse into the liquid present in the pressure chamber which causes the liquid to be ejected from the ejection opening at high pressure. The ejection pressure, and thus the volume or amount of liquid being ejected, may be precisely controlled by suitably adjusting the velocity of the drive member since said velocity determines the magnitude of the impact which is transmitted.

According to the ejection device described in EP 0 771 219, the volume of the pressure chamber considerably exceeds the stroke volume of the working piston so that a small, precisely dosed amount of liquid may be ejected regardless of the actual size of the pressure chamber.

To prevent the drive member from exerting any external force on the working piston after the impact has been transmitted, it is possible, for example, to stop the application of a driving force acting on the drive member towards the working piston as soon as the transmission of the impact starts, or to provide a stopper which prevents the drive member from exerting any force on the working piston after the impact has been transmitted.

The working piston is preferably made of a solid material which may transmit elastic shock waves with as little loss as possible, such as a metallic material. The drive member may be any impact-transmitting component, for example a drive piston, which may be accelerated within a drive pipe and is preferably coaxially aligned with the working piston. However, the drive member may also be designed other than as a piston, for example as a plate or a rocker arm which strikes on the working piston so that a driving impact is exerted thereupon.

The drive member may be moved pneumatically, hydraulically, mechanically, or electromagnetically, for example. The means driving the drive member may be designed such that they enable only a single working stroke of the drive member. However, the drive member may preferably be driven such that it successively transmits periodically repeated impact pulses so that the total amount of liquid being ejected may be controlled by suitably adjusting the number of repetitions. Preferably, the drive member is provided as a component which may be moved across an acceleration portion.

In the periodically operating ejection device described in EP 0 771 219, the working piston is returned to its starting position, i.e. the position it had prior to the elastic impact, after the liquid has been ejected, which is caused by the reflection of the elastic shock wave at the free end of the piston as well as by the reflection of the compression wave at the ejection end of the pressure chamber. The subsequent pressure drop in the pressure chamber resulting from said return motion causes liquid to be sucked into the chamber from a reservoir so that the device is immediately ready for the next ejection, thus enabling the successive ejection of predetermined doses of liquid.

The present invention provides an ejection device of the initially mentioned type which may be periodically operated independently of any liquid supply.

The ejection device according to the present invention is designed such that after the displacement of its leading end, the working piston is not returned to its starting position, i.e. the position it had before the transmission of the impact, but is progressively displaced into the pressure chamber by the repeated application of elastic impacts, with the distance of each single displacement being defined by the predetermined displacement stroke.

In the ejection device according to the present invention, the compression wave propagating through the working piston as the result of each impact transmitted thereto causes the working piston to be displaced into the pressure chamber by a certain distance, i.e. the predetermined displacement stroke, so that liquid is being ejected. The liquid supply is the amount of liquid initially present in the pressure chamber, which is then gradually squirted out from the pressure chamber. Thus, the pressure chamber of the ejection device according to the present invention is simultaneously used as a liquid supply chamber so that it is not necessary to provide an additional reservoir including supply lines to connect the reservoir to the pressure chamber, or any check valves to prevent the liquid in the pressure chamber from returning to the reservoir.

To prevent that the working piston reverses its motion and is pushed out of the pressure chamber as a result of the pressure increase in the pressure chamber and of the compression wave being to some extent reflected, which would result in air being sucked into the pressure chamber and thus render the operation of the device inaccurate, the masses of the movable components as well as the impact velocity of the drive member may be adjusted such that substantially the entire amount of impact strength is consumed for ejecting the liquid. Therefore, the frictional forces created between the working piston and its surrounding wall portions are sufficient to hold the working piston in its respective displaced position. Further, a check valve may be provided in the fluid connection between the pressure chamber and the ejection opening which enables the ejection of fluid while preventing air from being sucked into the pressure chamber. In this way, any reverse motion of the working piston is prevented.

Preferably, the ejection device according to the present invention is provided with linear reverse stopping means to support the working piston so that any reverse displacement thereof is prevented.

The linear reverse stopping means permit the movement of the working piston into the pressure chamber while blocking any reverse motion thereof caused by the compression wave being to some extent reflected at the end of the working piston facing the pressure chamber. In this way, the working piston is more reliably retained at the position it has at the end of the ejection process after the ejection process is over. Consequently, there is no risk of air being sucked into the pressure chamber through the ejection opening. Furthermore, the device is immediately ready for further use after each impact.

In most cases, it is not necessary to provide a check valve to control the ejection opening, because the continuous progression of the working piston excludes the risk of air being sucked into the pressure chamber through the ejection opening.

The total number of possible injections is determined by the maximum possible displacement of the working piston into the pressure chamber and by the adjusted working stroke of the working piston. The volume of liquid left in the pressure chamber at the time of the final working stroke should significantly exceed the volume of said final working stroke. The working stroke of the working piston may be adjusted via the impact transmitted by the drive member. The amount of liquid ejected by each working stroke is preferably in the range of approximately 5–10 $\mu$l.

The linear reverse stopping means are designed to allow the displacement of the working piston during its working stroke while any reverse motion thereof is prevented. The reverse stopping means may be designed to operate on the principle of a frictional locking mechanism, wherein the forward displacement of the working piston generates small frictional forces which may be overcome by the piston, whereas an attempted reverse motion of the working piston causes such an increase in frictional force that said reverse motion is prevented. Frictional locking means of this type may include a pivoting arm whose free end rests at the working piston. During the displacement of the working piston into the pressure chamber, said pivoting arm turns away from the working piston, whereas during any reverse motion of the working piston, the arm is pivoted and clamped against the working piston because of friction. Alternatively, the reverse stopping means may be designed as a ball-type locking mechanism comprising a ball which is accommodated between the working piston and a sleeve which has a conical inner shape and surrounds the working piston. The conical sleeve diverges towards the desired direction of displacement of the working piston so that when the piston moves in the opposite direction, the ball is wedged in between the working piston and the sleeve and, thus, prevent the piston from moving any further in said opposite direction. The reverse stopping means may also be designed as a ring made of fibrous material which is arranged around the working piston so that its fibers bend to lie closely on the surface of the working piston during the displacement of the working piston, whereas during a reverse motion of the working piston, the fibers straighten up and prevent any further reverse motion, similar to the operation of a ski having a scaled lower surface. Further, the reverse stopping means may be a positive locking mechanism such as a ratchet, a ball or roller mechanism or any other clamp-type locking mechanism, which may be used on its own or in combination with a frictional locking mechanism.

The ejection device according to the present invention is specially designed for the use as a medical instrument to eject liquid drugs. Therefore, it is important to minimize the risk of said liquid being contaminated in the pressure chamber of the device, which is why the pressure chamber has to be effectively sealed to prevent pathogens from infiltrating. For this purpose, the ejection opening may be covered by a cap, for example. For the working piston, however, this sealing problem cannot be solved as easily because the piston has to act in combination with the moving drive member for impact transmission, and is itself subject to displacement. As it is not possible to sufficiently sterilize all components of the driving mechanism, pathogens or impurities may infiltrate the pressure chamber via the working piston.

As a solution to this problem, the working piston may be provided with a single sealing element such as an O-ring or a lip seal, for example, to seal its circumference against the surrounding wall member. Said sealing element has the further advantage that it prevents the high-pressure pulse transmitted by the impact into the liquid from propagating rearwardly, i.e. in the reverse direction, through the gap between the working piston and its surrounding wall member, which would result in a pressure drop in the pressure chamber as well as in an undesired rearwardly directed ejection of liquid from the pressure chamber. Advantageously, the working piston is provided with two elastic sealing elements arranged at a distance from each other, which seal the circumference of the working piston against an associated wall member, with said distance between the two sealing elements being greater than the total working stroke of the working piston.

This has the advantage that any contamination of the working piston occurring on the drive member-facing side thereof, i.e. at the portion extending beyond the sealing element which is distal to the pressure chamber, cannot get across the sealing element proximal to the pressure chamber and into the pressure chamber. Said contaminated portion of the working piston could thus at most be displaced into the portion between the two sealing elements, which on their part sufficiently prevent the infiltration of pathogens.

In particular during the ejection process, when the pressure in the pressure chamber is very high, the sealing elements sealing the working piston against its surrounding wall member are subjected to increased stresses and strains so that the compression wave might get past the two sealing elements and propagate throug the gap formed between the working piston and its surrounding wall member, which would result in liquid leaking from the pressure chamber. The leaked liquid could then reach the components of the driving mechanism and damage or affect the proper functioning thereof.

To prevent this from happening, the working piston is preferably surrounded by a gas-filled annular chamber which is formed between the two sealing elements and serves as a compensation chamber. If the liquid gets past the sealing element proximal to the pressure chamber during the period of high pressure, its high pressure is reduced in the annular chamber so that it cannot get past the second sealing element. Further, the annular chamber absorbs any capillary forces which are generated in the gap between the working piston and the cylinder surrounding it.

According to an embodiment, an intermediary member is provided as a separate component between the working piston and the drive member, to transmit the elastic impact from the drive member to the working piston.

In this embodiment of the present invention, the impact is transmitted via the intermediary member which is acted upon by the drive member. When the drive member strikes upon the intermediary member, a shock wave is excited within the intermediary member which propagates therethrough and is transmitted by the intermediary member to the working piston which in turn transmits a high-pressure pulse into the liquid contained in the pressure chamber. By providing an intermediary member as described above, a number of advantageous variants of the ejection device according to the present invention are made possible. Thus, the intermediary member may be used to separately seal the components of the drive unit of the ejection device against the pressure chamber. For example, the acceleration portion across which the drive member is accelerated may be separately sealed against the pressure chamber so that the second sealing element to be advantageously provided at the working piston as described above may be dispensed with because the working piston is no longer subject to any potential contamination by the drive member.

The intermediary member also enables an option with respect to the provision of the reverse stopping means, which may be provided at the working piston and/or at the intermediary member. By providing the reverse stopping means at the intermediary member only, the working piston may be designed exclusively for its main purpose, i.e. as a piston delimiting the pressure chamber. Advantageously, the intermediary member is made of a solid material capable of transmitting elastic shock waves almost without loss, such as a metallic material. Preferably, this intermediary member also has the sole purpose of transmitting compression waves excited by the elastic impact. Further, the intermediary member is preferably designed as an intermediary piston which may be circumferentially sealed against a corresponding wall member by means of simple elastic sealing elements such as O-rings. In this case, the drive member is suitably designed as a driving piston which is movable in a drive pipe into which the intermediary piston extends in a sealing manner. Preferably, the motion of the intermediary piston is axially delimited by stoppers arranged on both sides thereof so that it is prevented from accidentally moving out of the drive pipe or too far into the drive pipe.

A further possible embodiment of the reverse stopping means engaging the intermediary piston in addition to the ones described above is a stuffing box which may be entered by the leading end of the intermediary piston. In this case, the compression wave propagating in the direction of the impact is strong enough to displace the leading end of the intermediary piston into the stuffing box by the predetermined working stroke. The displaced leading end remains lodged in the stuffing box so that the remaining portion of the intermediary piston is moved along automatically. To facilitate the movement of the intermediary piston into the stuffing box, the leading end of the piston is preferably inserted into the stuffing box before the device is put into operation.

Most preferably, the intermediary member abuts against the working piston without play so that there are no substantial energy losses caused by an initial acceleration and motion of the intermediary member. Therefore, the intermediary member should be able to move along with the working piston, i.e. it needs to be supported in a way that enables displacement. The movement of the intermediary member together with the working piston may be ensured, for example, by providing the reverse stopping means at the intermediary member, or at the intermediary member and at the working piston. Preferably, however, the working piston and the intermediary member are separably connected to each other by means of a coupling. In this way, it is possible to prevent even the slightest detachment of the working piston from the intermediary member, which could otherwise cause the two components to periodically strike against each other which would in turn interfere with the subsequent impact transmission. According to this embodiment, the linear reverse stopping means may also be provided such that they only abut against the working piston.

Instead of being carried along with the working piston during the displacement thereof, the intermediary member may also be adjusted stepwise in the axial direction towards the working piston after each displacement of the piston. For this purpose, the intermediary member is preferably designed such that it is displaceable by the drive member during impact transmission to the working piston, until it abuts against a stopper member which is in turn stepwise movable in the axial direction towards the working piston. The stopper member determines and limits the forward stroke of the intermediary member during impact transmission. In this way, the dosage of liquid being ejected can be adjusted as required. By adjusting the stopper member step by step, i.e. after each displacement of the working piston, it can be ensured that the dosage amount remains the same for each of the subsequent displacements of the working piston. However, the stopper member may also be adjusted after the transmission of several impacts.

Preferably, the impact of the drive member against the stopper member is reproducibly dampened to further increase the dosing accuracy. A simple, suitable dampening means is an elastic buffer having a predetermined spring characteristic, which is arranged between the drive member and the intermediary member.

The adjustment of the stopper member may be performed by means of threads, for example, which are engaged by the stopper member to enable the screw-type adjustment thereof. Preferably, a spring is provided to support the stopper member at the threads without play so that the dosing accuracy will not be affected by the inevitable backlash of the threads.

For adjusting the stopper member, and preferably also the intermediary member, it is possible to use the drive pipe wherein the drive member is accommodated as a reciprocating drive piston. For this purpose, the drive pipe is designed to be suitably adjustable as well.

The adjustment of the intermediary member and/or stopper member may be performed manually or, preferably, by means of a stepper drive which has a predetermined, if necessary adjustable step.

Although there are various possible embodiments of the linear reverse stopping means as described above, they are preferably comprised of at least one elastic sealing element which seals the circumference of the working piston or of the intermediary member against their associated surrounding wall member.

This dual function of the sealing element obviates the need for several additional components of the linear reverse stopping means. The sealing element may in particular be a lip seal whose sealing lip is inclined towards the moving direction of the working piston. When the working piston tends to move away from the pressure chamber, the sealing lip inclined in the above mentioned way is moved along with the working piston against its natural inclination due to the friction occurring between the working piston and the sealing lip so that the lip is increasingly forced against the working piston and thus prevents any further displacement of the piston away from the pressure chamber. However, when the working piston starts to move towards the pressure chamber, there is nearly no increase in the pressure applied on the working piston by the sealing lip, so that the working piston may be displaced relative to the sealing element. Thus, the sealing lip functions similarly to the above described pivoting arm. The locking effect of the sealing lip may be further improved by flutes provided at the working piston, for example in the form of circumferential grooves which are spaced apart from each other in the axial direction of the piston and whose depth is so small that they do not affect the sealing action of the lip seal. Further, a plurality of said annular lip seals may be used as a packing. Alternatively, an O-ring may be arranged between the working piston and its associated wall member, or between the piston-shaped intermediary member and its associated wall member, with said O-ring being biased such that the desired linear reverse stopping effect is achieved.

If said sealing rings are designed and used in such a way that they act both as reverse stopping means and as sealing elements, they may obviate the need for additional sealing elements.

If an intermediary member is used, an advantageous multipart version of the linear reverse stopping means comprises at least two elastic sealing elements, with each sealing element sealing the circumference of one of the working piston and the intermediary member against their associated wall members.

As may be gathered from the above description, the intermediary member is to be used preferably in such a way that it also functions as a seal against the portion of the device which comprises the driving components. Therefore, it is obvious to provide the intermediary member with a sealing element as described above which at the same time functions as a reverse stopping member so that respective additional components may be dispensed with. The same applies to a sealing element preferably provided at the working piston. Thus, an improved operation of the linear reverse stopping means may be achieved without providing additional components.

Advantageously, the reverse stopping means may be disengaged so that the working piston and the intermediary member, respectively, may be returned to their original position against the action of the reverse stopping means after the working piston has moved into the pressure chamber. If a sealing element is used as the reverse stopping member, it may be designed to be removable from the inserted working piston or intermediary member, for example.

According to a preferred embodiment, the linear reverse stopping means comprise an O-ring as a sealing element, with said O-ring being axially compressible by means of an axially adjustable clamping ring wherein the working piston or the intermediary member is received, and with the axial compression of said O-ring producing a radial pressure against the working piston and the intermediary member, respectively.

The above embodiment has the advantage that the working piston and the intermediary member, respectively, may be easily inserted into the O-ring during assembly, as well as easily removed therefrom during disassembly. By adjusting the clamping ring, the pressure produced by the O-ring is being increased until the desired reverse stopping characteristics are achieved. Preferably, the clamping ring is provided with a stopper up to which the clamping ring is to be moved to compress the O-ring so that the adjustment of the suitable contact pressure is not left to the user. After the working piston has moved into the pressure chamber by the respectively predetermined maximum distance, the clamping ring may be released so that the working piston may easily be removed to enable the cleaning, sterilization or refilling, if necessary, of the pressure chamber.

Preferably, the above explained linear reverse stopping means comprise another O-ring which is axially spaced apart from the first O-ring via a distance sleeve arranged adjacent to the clamping ring and surrounding the working piston and the intermediary member, respectively. Said other O-ring may be axially compressed by the axially displaceable clamping ring via the distance sleeve acting as a power transmitting member, so that it exerts a radial pressure on the working piston or the intermediary member.

This design enables the linear reverse stopping means to advantageously comprise two sealing elements as described above, which are arranged at either the working piston or the intermediary member with only one adjustable clamping ring being required. This embodiment of the linear reverse stopping means is therefore particularly suitable for an embodiment of the device which does not comprise an intermediary member and is provided with two sealing elements spaced in the longitudinal direction of the working piston. In addition, the above described advantageous annular chamber between the two sealing elements may be easily provided within the distance sleeve.

However, the above sealing structure comprising the clamping ring as well as the axially compressible O-ring(s) is advantageous and used as the preferred sealing structure—in particular for sealing the working piston against its associated wall member—regardless of whether or not it is simultaneously used as reverse stopping mechanism because it reasonably prevents the compression wave from propagating through the gap formed between the working piston and its associated wall member.

The ejection device according to the present invention may be designed as an integral disposable device, for example, which is provided with a pneumatic drive comprising a compressed-air cartridge which is incorporated into the device and contains a suitable amount of compressed air to act on the drive member for the desired maximum number of ejections. Preferably, however, the ejection device is divided into a head unit comprising the working piston and at least a portion of the pressure chamber, and a drive unit comprising the drive member and the intermediary member, if desired. The head unit and the drive unit of the device are formed as independent, separate units which are connected to each other by a separable coupling.

This configuration enables the drive unit to be designed as a permanent base unit, whereas the head unit may be designed as an exchangeable disposable unit or as a removable refillable unit, for example. In said latter version, the head unit may simply be removed from the drive unit, after which the piston may be removed from the pressure chamber so that said chamber may be refilled. The coupling between the head unit and the drive unit may be designed, for example, as a screw-type or plug-in connection, or as a bayonet fastener. The divided ejecton device comprising a head unit and a drive unit has the further advantage that the drive unit of the device may be sterilized separately and as a whole unit within a sterilizer.

The pressure chamber may be formed exclusively in the head unit, for example, which in this case also comprises the ejection opening.

Preferably, the pressure chamber comprises a cavity formed in the head unit, with said cavity forming at least a portion of the pressure chamber and accommodating the working piston. Further, the working piston as well as the cavity formed in the head unit are advantageously designed such that only a small amount of residual liquid remains in the cavity when the working piston has reached its end position, i.e. when it has moved into the pressure chamber so that it abuts against the bottom of the cavity. For this purpose, the bottom of the cavity is preferably shaped such that it conforms with the opposing end face of the working piston so that said end face of the working piston has a positive fit at the bottom of the cavity.

The head unit may have an ejection nozzle or an endoscopic catheter attached thereto which communicate with the cavity via a fluid communication. The pressure chamber is constituted by the liquid passage formed within the ejection nozzle or the endoscopic catheter, and by the cavity formed in the head unit. The endoscopic catheter may be designed as a rigid or flexible catheter. Further, the endoscopic catheter may be formed such that it may be inserted into the working passage of an endoscope. For endoscopic applications, the ejection device and the endoscope are preferably combined to form a single unit.

Further, the head unit may be provided with a window or display portion which indicates the position of the working piston so that the current level of liquid contained in the pressure chamber may be read.

If an intermediary member is provided, the head unit and the drive unit are to be assembled such that the working piston sits closely at the intermediary member, or vice versa. For this purpose, the coupling between the working piston and the intermediary member is advantageously fixed at the intermediary member and designed such that, it is automatically connected with the working piston during their assembly so that the gap between the working piston and the intermediary member is closed. In the case of a piston-shaped intermediary member, the coupling is advantageously formed as a coupling sleeve so that the working piston and the intermediary piston may snap into said sleeve. During assembly, the coupling sleeve is first fixed to either the working piston or the intermediary piston, after which the components are joined by gradually engaging the sleeve into the intermediary piston and the working piston, respectively, so that a connection is formed between them.

Preferably, the components of the head unit which delimit the pressure chamber are to be sufficiently sterilized, and must be kept sterile. Therefore, they are provided with particularly smooth outer surfaces, for example, which foreclose the accumulation of impurities. Moreover, the materials of these components should be inert with respect to the liquid to be ejected so that they will not be damaged.

If the head unit is to be refillable, a filling device is provided by means of which the volume of the pressure chamber may be precisely adjusted so that the pressure chamber may be precisely refilled. Said filling device comprises a U-shaped frame, with one leg of the frame forming a horizontal base and the other leg forming a horizontal support member for the head unit, the base being connected with the support member by the vertical web of the frame. The head unit may be held by the support member in such a way that the working piston accommodated therein is vertically movable to adjust the volume of the pressure chamber, and that the end face of the working piston facing away from the pressure chamber may abut against the base of the frame. Thus, the base forms a stopper limiting the movement of the working piston so that the volume of the pressure chamber is precisely defined. The liquid may, for example, be filled into the pressure chamber before the volume thereof is precisely adjusted, so that a portion of the liquid is forced out of the ejection opening during adjustment. If an ejection nozzle or endoscopic catheter is attached to the head unit, it may be removed to allow the liquid to be filled into the cavity through a liquid outlet formed in the head unit. The frame may be elongated in a direction perpendicular to its U-shaped cross section so that a plurality of head units arranged at a distance from each other may be fixed to the support member in the longitudinal direction thereof, and may thus be simultaneously refilled.

This embodiment is particularly advantageous when the drive unit comprises an intermediary member. Prior to assembly, the intermediary member is returned to its original or starting position so it forces the working piston a little bit into the pressure chamber during assembly, which results in some liquid being displaced from the pressure chamber through the ejection opening. In this way, any gas bubbles may be forced out of the device prior to its operation, similar to the venting of a medical syringe.

According to a preferred embodiment, the drive member is designed as a pneumatically movable drive piston which is arranged in a drive pipe. From its starting position, the drive piston is simply accelerated by means of compressed air to move towards the working piston. The drive pipe is provided with at least one through hole formed in its end portion proximal to the working piston and connecting the interior of the drive pipe with a venting chamber so that the compressed air displaced by the working piston during its movement into the pressure chamber may be vented. The drive member is returned to its starting position by means of the air vented into the venting chamber. The vented air is compressed in the venting chamber and may flow back into the drive pipe via said through hole so that it forces the drive piston back to its original position. The through hole is arranged such that it coincides with the gap formed between the working piston and the drive piston at any time during the operation of the ejection device. Because said gap is continually displaced towards the pressure chamber by the successive motion of the working piston, the through hole is preferably formed as a longitudinal slot whose length is defined according to the required total working stroke. However, according to a preferred embodiment, the total working stroke is defined by the length of the longitudinal slot, because the air in the venting chamber can only flow back into the drive pipe until the end of the drive piston facing the working piston reaches the working piston-facing end of the longitudinal slot so that the drive piston seals the slot from the inside Therefore, the length of the slot precisely defines the distance to be travelled by the working piston.

Preferably, the cavity containing the liquid is at any time larger than the stroke volume of the working piston, i.e. also during the final working stroke, so that the ejection of the precise amount of liquid as defined by the predetermined displacement stroke is ensured even during the final working stroke of the working piston. This may be easily achieved by accordingly adjusting the length of the longitudinal slot, for example. However, it is also possible to allow the working piston to travel into the cavity until it abuts against the end face thereof. In this case, the length of the cavity is to be designed such that the required amount of liquid is ejected during the final working stroke, i.e. until the working piston abuts.

To prevent the drive member from accidentally leaving its starting position, a holding device is provided to hold the drive member at its starting position. The holding device may be a clamping device, for example, which holds the drive member by means of clamping forces which may be overcome by the driving forces. Advantageously, a magnetic holding device is provided to hold the drive member and formed, for example, by an electromagnet, but preferably by a permanent magnet. The drive member may have a magnetic part attached thereto, for example a magnetizable metallic member, which acts in combination with the magnetic holding means. Preferably, the entire drive member is made of a magnetizable material such as steel, for example.

Figure 2:
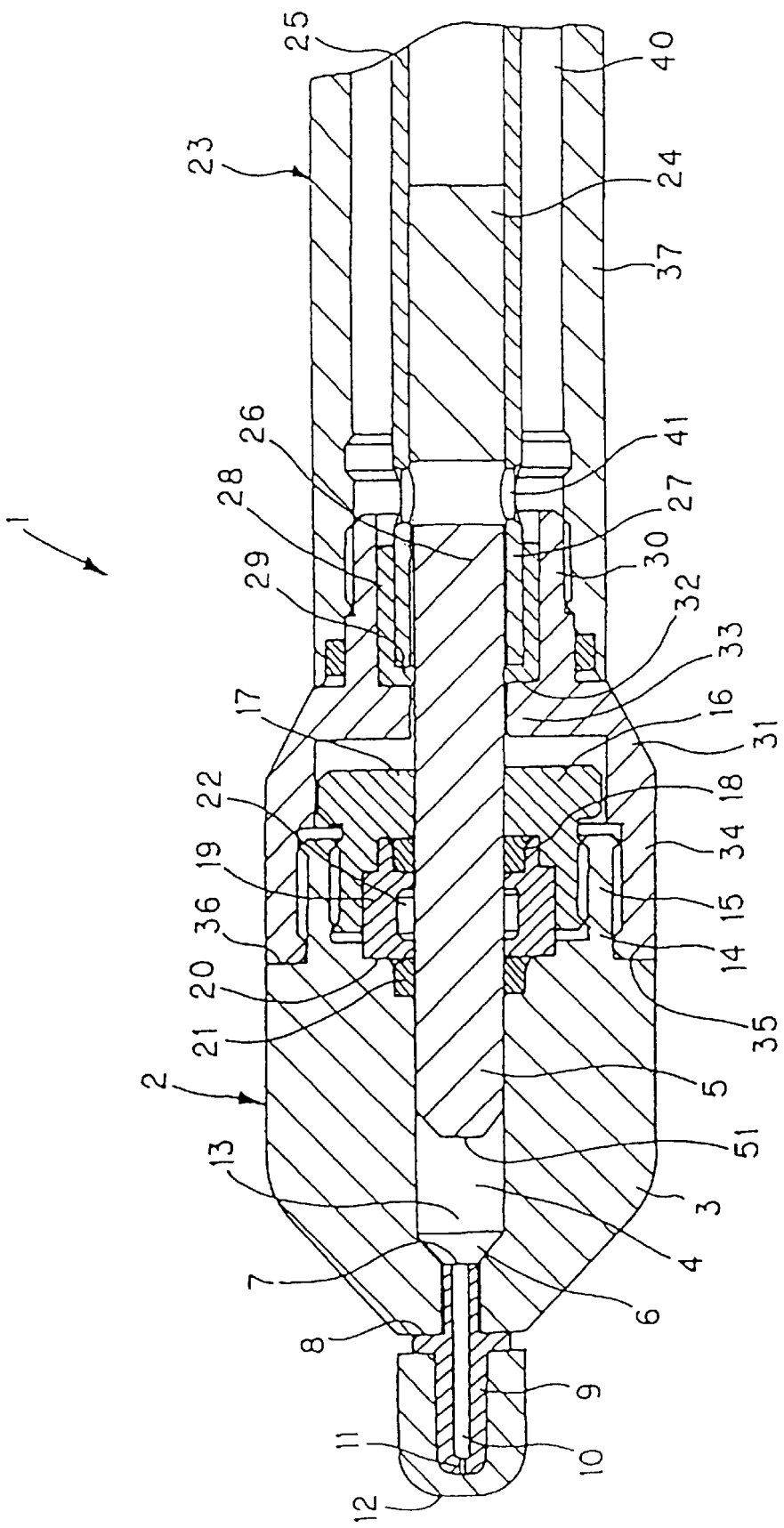
Figure 3:
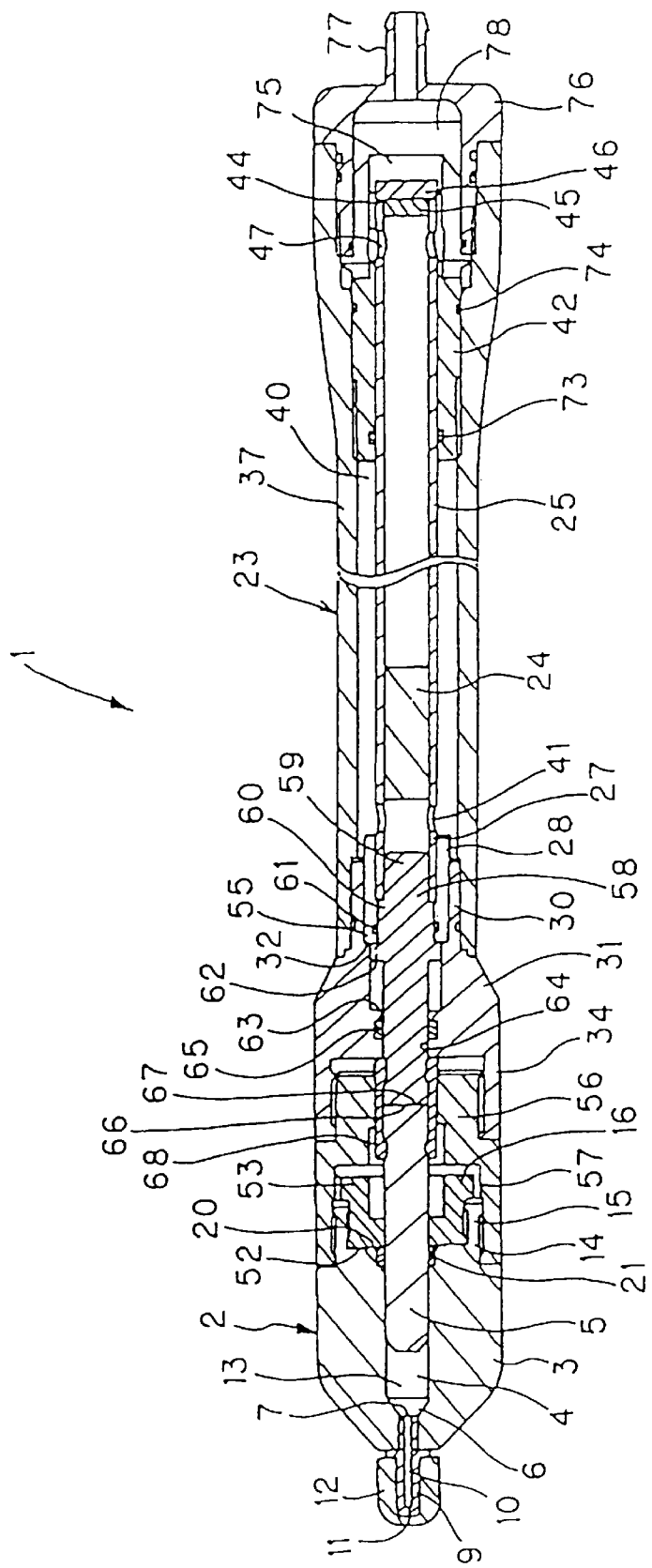
Figure 4:
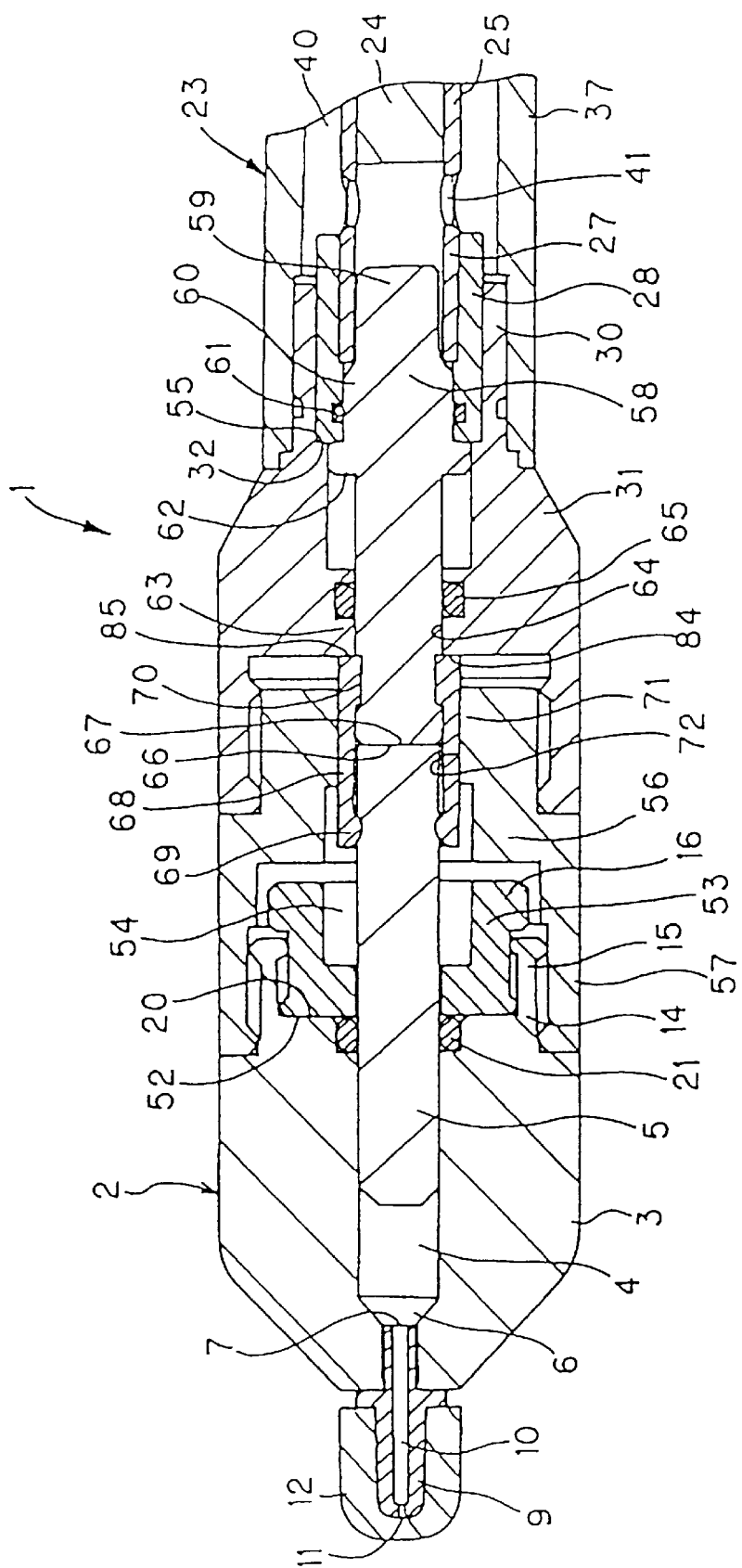
Figure 6:
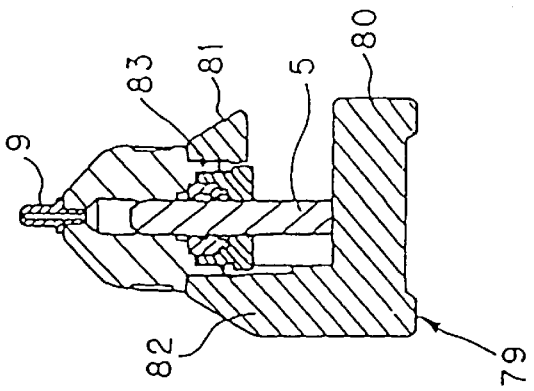
Figure 5:
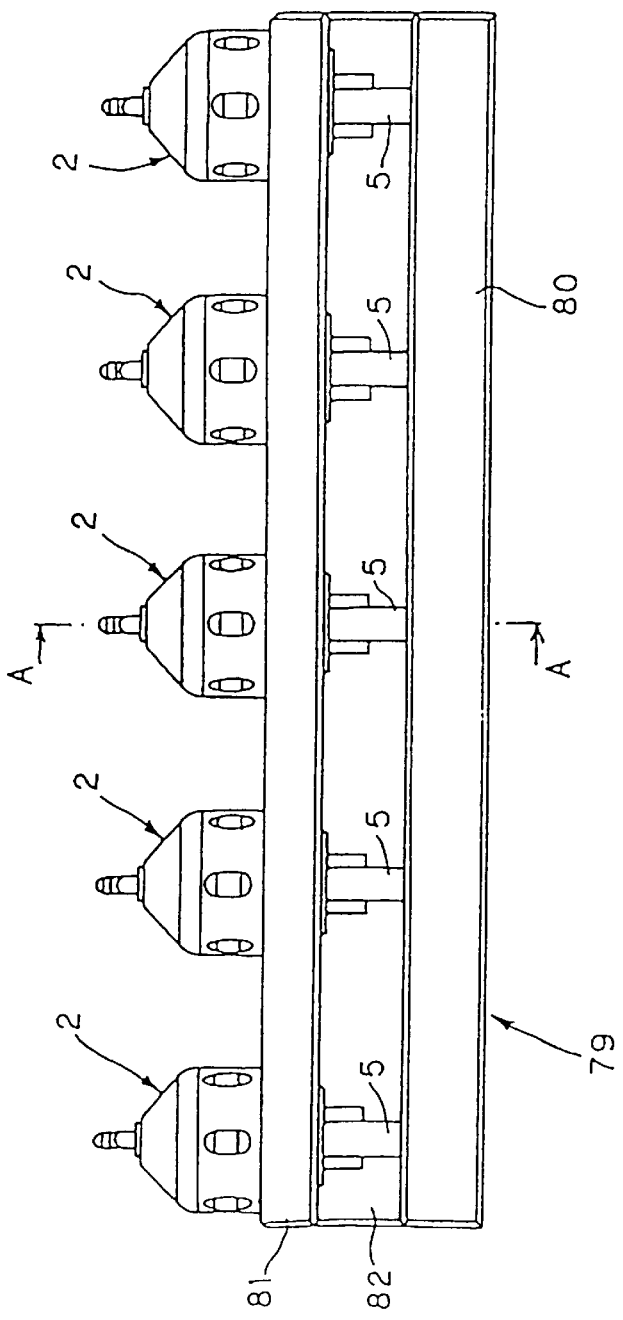
Figure 7:
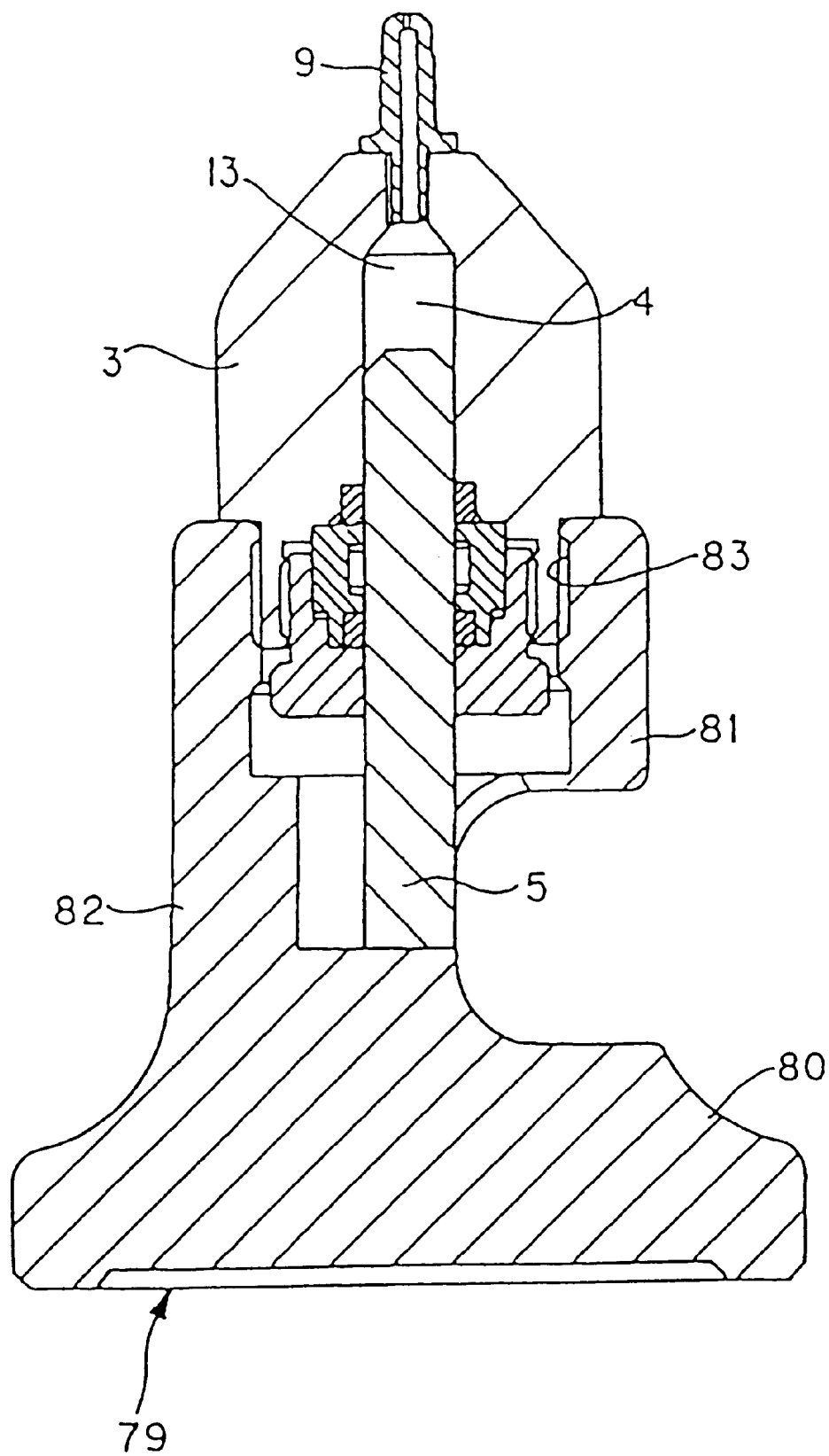
Figure 8:
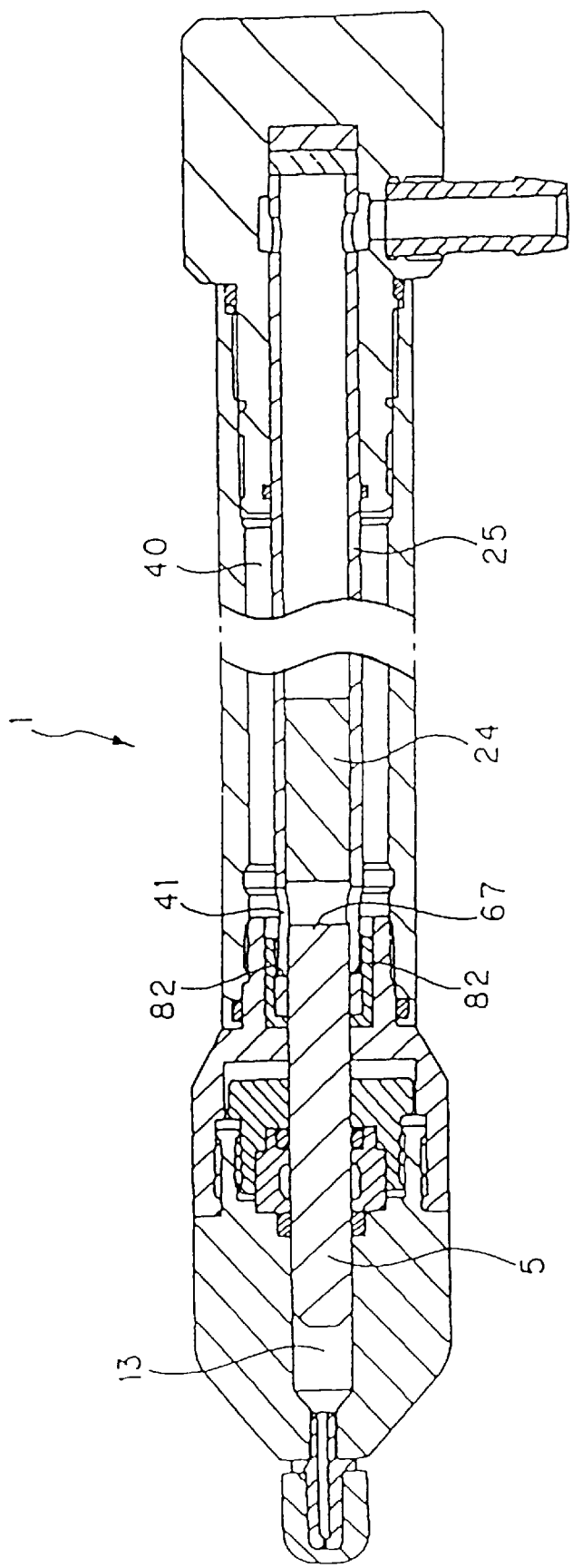
Figure 9:
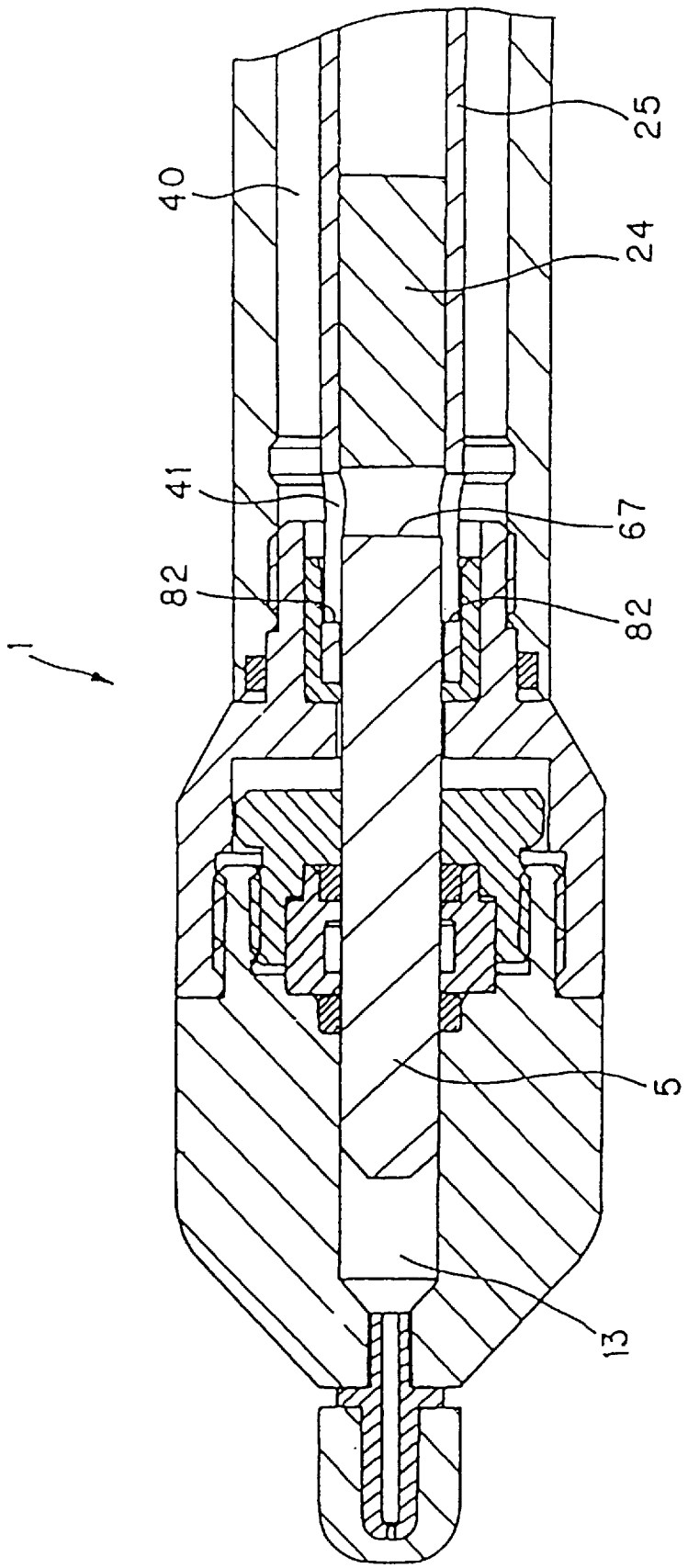
Figure 10:
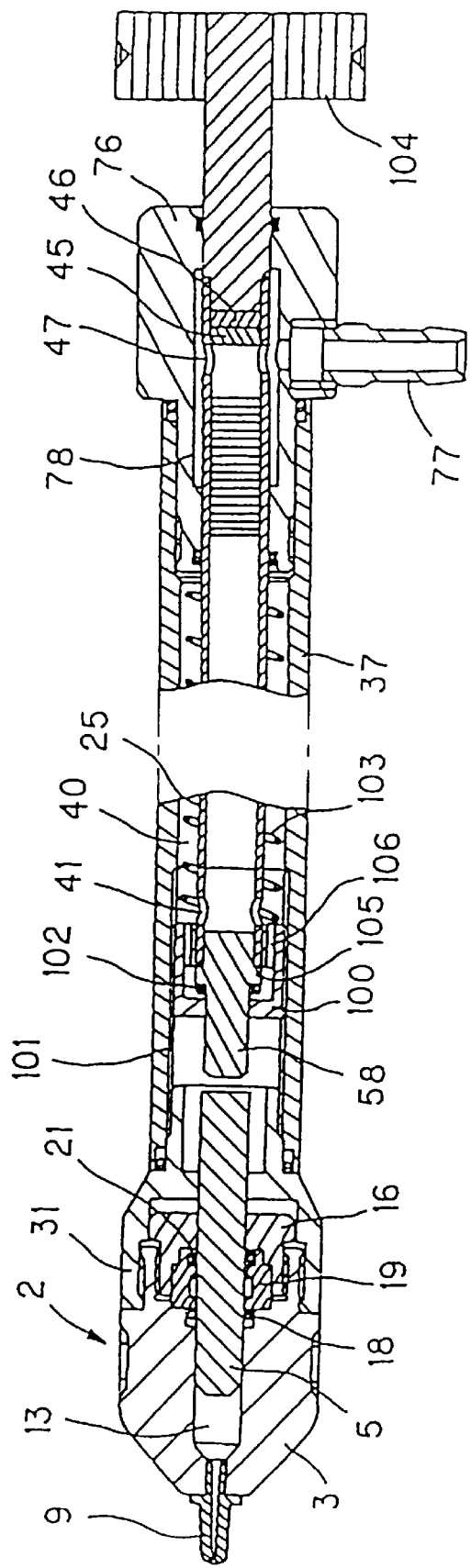

The present invention will now be explained in more detail by means of preferred embodiments thereof and with reference to the accompanying drawing, wherein FIG. 1 shows a longitudinal section of an ejection device for the high-pressure ejection of liquids according to an embodiment of the present invention, FIG. 2 shows an enlarged view of the front portion of the ejection device according to FIG. 1, FIG. 3 shows a longitudinal section of an ejection device for the high-pressure ejection of liquids according to another embodiment of the present invention, FIG. 4 shows an enlarged view of the front portion of the ejection device according to FIG. 3, FIG. 5 shows a front view of a filling device, with the head units of the ejection device according to the present invention being inserted therein, FIG. 6 shows a section along the line A—A in FIG. 5, FIG. 7 shows a section similar to that in FIG. 6 of a filling device according to the present invention, FIG. 8 shows a longitudinal section of an ejection device for the high-pressure ejection of liquids according to another embodiment of the present invention, FIG. 9 shows an enlarged view of the front portion of the ejection device according to FIG. 8, and FIG. 10 shows a longitudinal section of an ejection device for the high-pressure ejection of liquids according to yet another embodiment of the present invention.

Throughout the figures, like parts are referred to by the same reference signs.

FIGS. 1 and 2 each show a longitudinal section of an ejection device 1 for the high-pressure ejection of liquid according to the present invention. The ejection device 1 comprises a head unit 2 having a head unit body 3 wherein a cylindrical cavity 4 is formed. In said cavity 4, a working piston 5 is received to be axially movable. The cavity 4 is conically tapered at its end portion 6 facing away from the working piston and opens into an outlet 7. A nozzle 9 formed as a substantially cylindrical, short pipe is threaded into the end face 8 facing away from the working piston of the head unit body 3. In said nozzle 9, a passage 10 is formed which communicates with the cavity 4 via the outlet 7 and opens into an ejection opening 11. Adjacent to the ejection opening 11, the passage 10 is formed with a smaller diameter than in its remaining portion so that a nozzle effect is achieved. Preferably, the diameter of the ejection opening 11 is 0.3 mm. A cap 12 is arranged on the nozzle 9 so that the ejection opening 11 is covered. The cavity 4 formed in the head unit body 3 and the passage 10 formed in the nozzle 9 constitute a pressure chamber 13 which is axially delimited by the working piston 5.

The head unit body 3 has an annular flange 15 formed at its end portion 14 facing away from the nozzle 9, which annular flange 15 is provided with an axially extending external thread as well as with an internal thread coaxial to the former. A clamping ring 16 surrounding the working piston 5 and having a matching external thread is threaded into the annular flange 15, said clamping ring 16 further comprising an inwardly facing annular flange 17 whose side facing the pressure chamber 13 presses against an O-ring 18 arranged around the circumference of the working piston 5. Said O-ring 18 is received in an inner circumferential groove formed in a distance sleeve 19 that is arranged around the working piston 5 and received in the clamping ring 16. The inwardly facing annular flange 17 of the clamping ring 16 axially pressurizes the distance sleeve 19 towards the pressure chamber 13 so that it is pressed against both an inner surrounding shoulder 20 of the body 3 and another O-ring 21 arranged around the circumference of the working piston 5. Said O-ring 21 is accommodated in an inner annular groove formed in the head unit body 3 at a position adjacent to the inner shoulder 20. By threadingly displacing the clamping ring 16 in the axial direction towards the O-rings 18, 21, the radial pressure exerted on the working piston 5 by the O-rings 18, 21 may be increased. The clamping ring 16 may be displaced until the end face of the distance sleeve 16 abuts against the stop formed by the inner shoulder 20 of the head unit body 3. The axial displacement range of the clamping ring 16 is chosen such that when the distance sleeve 19 abuts against the shoulder 20, the O-rings 18, 21 have a linear reverse stopping effect on the working piston 5, as will be explained later in more detail. The distance sleeve 19 is provided with an inner annular groove 22 which is formed at a position between the two O-rings 18, 21 and opens towards the working piston 5 so that it defines an annular chamber surrounding the working piston 5 at a position between said O-rings 18, 21.

The sealing structure provided at the head unit body 3 and comprising the clamping ring 16, the distance sleeve 19 and the O-rings 18, 21 is also part of the head unit 2 which is separably mounted to a drive unit 23 driving the working piston 5, as will be explained afterwards.

The drive unit 23 comprises a drive member formed by a cylindrical drive piston 24 which is freely movable in the longitudinal direction of a cylindrical drive pipe 25. The drive pipe 25 and the drive piston 24 received therein are arranged to be coaxial with the working piston 5 whose end portion 26 facing away from the pressure chamber extends into the drive pipe 25. The drive pipe 25 has a stuffing box 28 arranged on its end portion 27 facing towards the pressure chamber 13, with said stuffing box 28 comprising an inwardly facing annular flange 29 that abuts against the drive pipe 25. The stuffing box 28 is received in a receiving sleeve 31, i.e. in an end portion 30 thereof facing away from the head unit body 3, with its end face 32 facing towards the head unit body 3 abutting against an inwardly facing annular flange 33 of the receiving sleeve 31. The receiving sleeve 31, which is also part of the drive unit 23, is provided with an axially extending internal thread formed at its end portion 34 facing towards the head unit body 3, and is threaded onto the annular flange 15 of the head unit body 3 by means of said thread. The pressure chamber-facing end face 35 of the receiving sleeve 31 is circumferentially flush with a shoulder 36 of the body 3.

Thus, the separable connection between the head unit 2 and the drive unit 23 is formed by a screw-type connection between the annular flange 15 formed at the head unit body 3, and the receiving sleeve 31.

The receiving sleeve 31 comprises an axially extending external thread at its end portion 30 facing away from the head unit body 3. A cylindrical receiving pipe 37 designed as a casing to accommodate the drive pipe 25 has an axially extending inner thread formed at its end portion 38 facing towards the head unit body 3, and is threaded onto the end portion 30 of the receiving sleeve 31 via an O-ring 39 that forms a circumferential seal.

An annular chamber 40 is formed between the receiving pipe 37 and the drive pipe 25 and communicates with the interior of the drive pipe 25 via lateral openings 41 formed in the drive pipe 25 at positions adjacent to the stuffing box 28.

At its end facing away from the head unit 2, the annular chamber 40 is axially delimited by a sealing bush 42 which surrounds the drive pipe 25 and is axially threaded into the receiving pipe 37. O-rings 39, 40 are provided to seal the sealing bush 42 against the drive pipe 25 and the receiving pipe 37, respectively. A plug 43 formed integrally with the sealing bush 42 sealingly closes both the end of the receiving pipe 37 facing away from the head unit 2 and the end of the drive pipe 25 facing away from the head unit 2. A rigid plate 45 and an elastic plate 46 are arranged between the end face 44 of the drive pipe 25 and the plug 43 and act together as a buffered stop for the drive piston 24 at the end thereof distal to the head unit. The two plates 45, 46 are arranged one after the other, with the rigid plate 45 being closer to the working piston 5. Advantageously, the plates 45, 46 have magnetic properties, and the working piston is made of a magnetizable material such as a magnetizable steel, so that the working piston is reliably held in its starting position at the plate 45 by magnetic forces and, thus, secured against accidental movement. To enable the operation of the ejection device, the magnetic forces are chosen such that they are smaller than the driving forces. The drive pipe 25 is provided with lateral openings 47 formed adjacent to its end closed by the plug 43. A through hole 48 having an inner thread is formed in the plug 43 at a lateral position coinciding with the openings 47, with a connecting piece 49 for the supply of compressed air being threaded into said through hole 48. The through hole 48 communicates with the openings 47 via an annular passage 50 formed in the plug 43 so that it surrounds the drive pipe 25 at the axial position of the openings 47.

Next, the operation of the above described ejection device 1 will be explained. Via the connecting piece 49, the ejection device 1 is supplied with compressed air delivered by a pump (not shown). Via the annular passage 50 and the openings 47, the compressed air enters the interior of the drive pipe 25 where it acts upon the drive piston 24 so that the latter is accelerated towards the working piston 5. The air which is displaced from the drive pipe 25 by the drive piston 24 is forced through the openings 41 and into the annular chamber 40. The drive piston 24 is accelerated, i.e. moved by a force created by the supplied compressed air, until it abuts against the working piston 5. Then, the air which has been compressed in the annular chamber 40 flows back into the drive pipe 25 through the openings 41 and, thus, forces the drive piston 24 back to its original position.

When the drive piston 24 abuts against the working piston 5 it excites a compression wave which propagates through the working piston 5 so that the end thereof facing the pressure chamber 13 is displaced into the cavity 4. As a result, the pressure in the pressure chamber 13 increases so that the liquid contained therein is squirted out from the ejection opening 11 at a very high speed.

The O-rings 18, 21 provided around the circumference of the working piston 5 to seal the pressure chamber 13 at its side facing the working piston are pressed against the working piston 5 by the threadingly adjustable clamping ring 16 so that the working piston 5 may be displaced into the pressure chamber 13, i.e. into the cavity 4—or to the left, according to FIG. 1—by the impact caused by the drive piston 24, but cannot be displaced in the reverse direction, i.e. out of the cavity 4 of the pressure chamber 13, by the reflected compression wave which is weaker than the incident one. Thus, the working piston 5 travels a certain distance to the left and into the pressure chamber 13 upon each impact transmitted thereon by the drive piston 24, with a small amount of liquid being ejected during its motion, and is held at its new position due to the linear reverse stopping effect achieved by means of the O-rings 18, 21 until the drive piston 24 abuts again. The O-rings 18, 21 pressed radially against the working piston 5 form linear reverse stopping means that operate according to the principle of a frictional locking mechanism.

At its end face 51 facing the cavity 4, the working piston 5 is conically tapered to conform with the cavity's end portion 6 facing away from the working piston so that the working piston 5 fits positively against the bottom of the cavity 4. In this way, it is ensured that the entire amount of liquid contained in the cavity 4 is ejected.

FIGS. 3 and 4 show an ejection device 1 for the high-pressure ejection of liquids according to another embodiment of the present invention.

The ejection device 1 according to this embodiment comprises a head unit 2 having a head unit body 3 wherein a cylindrical cavity 4 is formed. In said cavity 4, a working piston 5 is received to be axially movable, which in turn delimits the cavity 4 in the axial direction. The cavity 4 is conically tapered at its end portion 6 facing away from the working piston and opens into an outlet 7. As has already been described with reference to FIGS. 1 and 2, the head unit body 3 is provided with a nozzle 9 having an ejection opening 11 and being covered by a removable cap 12. As has also been described with reference to FIGS. 1 and 2, a pressure chamber 13 is comprised of the cavity 4 formed in the head unit body 3 and of a passage 10 formed in the nozzle 9, with said pressure chamber 13 being axially delimited by the working piston 5. The head unit body 3 has an annular flange 15 formed at its end portion 14 facing away from the nozzle 9, which annular flange 15 is provided with an axially extending external thread as well as with an internal thread coaxial to the former.

A clamping ring 16 surrounding the working piston 5 and having a matching external thread is threaded into the annular flange 15 whose end face 52 facing the pressure chamber 13 presses against an inner annular shoulder 20 formed at the head unit body 3 as well as against an O-ring 21 arranged around the circumference of the working piston 5. Said O-ring 21 is received in an inner circumferential groove formed in the head unit body 3 at a position adjacent to said inner shoulder 20.

The sealing structure comprising the clamping ring 16 and the O-ring 21 is also part of the head unit 2.

By threadingly displacing the clamping ring 16 in the axial direction towards the O-ring 21, the radial pressure exerted on the working piston 5 by the O-ring 21 is increased. As already explained with reference to FIGS. 1 and 2, the maximum axial displacement of the clamping ring 16, i.e. the distance it may travel until it abuts against the inner shoulder 20 of the head unit body 3, is chosen such that the O-ring 21 has a linear reverse stopping effect on the working piston 5. At its end portion 53 facing away from the O-ring 21, the clamping ring 16 is provided with an annular recess 54 which opens towards the working piston 5 so that it defines an annular chamber surrounding the working piston 5.

The ejection device 1 further comprises a drive unit 23 having a cylindrical drive piston 24 which is freely movable in the longitudinal direction of a cylindrical drive pipe 25. The drive unit 23 and the head unit 2 are separably mounted to each other, as will later be described in more detail. The drive pipe 25 and the drive piston 24 received therein are arranged to be coaxial with the working piston 5. The drive pipe 25 has a stuffing box 28 arranged on its end portion 27 facing towards the head unit body 3. The stuffing box 28 is received in a receiving sleeve 31, i.e. in an end portion 30 thereof facing away from the head unit body 3, with an outer circumferential portion of its end face 32 facing towards the head unit body 3 abutting against an inner shoulder 55 of the receiving sleeve 31. The receiving sleeve 31, which is also part of the drive unit 23, is provided with an axially extending internal thread formed at its end portion 34 facing towards the head unit body 3, and is sealingly threaded onto an intermediary sleeve 56 which comprises a matching external thread. Said intermediary sleeve 56 is provided with an internal thread formed at its end portion 57 facing towards the head unit body 3, and is sealingly threaded onto the annular flange 15 of the head unit body 3. The head unit body 3, the receiving sleeve 31 and the intermediary sleeve 56 are coaxially arranged with their adjacent circumferential edges being flush with each other.

Thus, the separable connection between the head unit 2 and the drive unit 23 is formed by a screw-type connection between the annular flange 15 formed at the head unit body 3, and the intermediary sleeve 56 which is part of the drive unit 23.

The drive unit 23 further comprises an intermediary member 58 partially accommodated in the receiving sleeve 31, which is substantially formed as a cylindrical intermediary piston and is arranged coaxially between the working piston 5 and the drive piston 24. At its end portion 59 facing away from the pressure chamber 13, the intermediary member 58 extends into the drive pipe 25 with a small radial play remaining between them, whereas a portion 60 thereof which is adjacent to the end portion 59 and larger in diameter than the latter extends into the stuffing box 28 almost without radial play. An O-ring 61 surrounding the intermediary member 58 is provided between the portion 60 and the stuffing box 28. The intermediary member 58 is provided with an outwardly facing annular flange 62 whose side facing away from the head unit body 3 abuts against the inner circumferential edge portion of the proximal end face 32 of the stuffing box 28 when the pressure chamber 13 is completely filled with liquid. The receiving sleeve 31 has an inwardly facing annular flange 63 forming a through hole 64 wherein the intermediary member 58 is accommodated almost without radial play so that it is axially guided therein. The annular flange 63 is provided with an annular groove which opens towards the intermediary member 58 and has an O-ring 65 arranged therein which seals the circumference of the intermediary member 58 against the receiving sleeve 31. The inwardly facing annular flange 63 is arranged at an axial distance from the pressure chamber-facing end face 32 of the stuffing box 28 and extends towards the head unit body 3 so that it defines an axial stopper proximal to the pressure chamber for the radial annular flange 62 formed at the intermediary member 58, which abuts against the inwardly facing annular flange 63 of the receiving sleeve 31 when the working piston 5 is maximally displaced into the cavity 4.

At its end face 66 facing the working piston 5, the intermediary member 58 abuts against the opposing end face 67 of the working piston 5, with the two components being separably connected with each other by a coupling sleeve 68 which surrounds said two end faces 66, 67. As may be seen from FIG. 4, the coupling sleeve 68 comprises two inwardly facing annular flanges 69, 70 which are each arranged on one side thereof and engage into corresponding annular grooves formed in the working piston 5 and the intemediary member 58, respectively. The coupling sleeve 68 is made of an elastic material so that it may be snapped onto the working piston 5 and the intermediary member 58. The annular flange 69 connecting the working piston 5 and the coupling sleeve 68 with each other is radially tapered towards the working piston 5 so that the locking force between these two components is weaker than that between the intermediary member 58 and the coupling sleeve 68, where the associated annular flange 70, as seen in its radial direction, is slightly axially expanded towards the working piston 5 or extends at least perpendicularly thereto, with the associated annular groove in the intemediary member 58 being slightly axially expanded towards the working piston 5, or extending perpendicularly thereto. As shown in FIG. 4, the intermediary sleeve 56 has an inwardly facing annular flange 71 which forms a through hole 72 wherein the coupling sleeve 68 is received almost without radial play so that it is axially guided therein.

The receiving sleeve 31 has a casing sealingly arranged at its end portion 30 facing away from the head unit body 3, which casing is part of the drive unit 23 and formed by a cylindrical receiving pipe 37 to accommodate the drive pipe 25 therein. An annular chamber 40 is formed between the receiving pipe 37 and the drive pipe 25 and communicates with the interior of the drive pipe 25 via openings 41 formed laterally in the drive pipe 25 at a position adjacent to the stuffing box 28.

At its end facing away from the head unit 2, the annular chamber 40 is axially delimited by a sealing bush 42 which surrounds the drive pipe 25 and is axially threaded into the receiving pipe 37. O-rings 73, 74 seal the sealing bush 42 against the drive pipe 25 and the receiving pipe 37, respectively. The end of the drive pipe 25 facing away from the head unit 2 is closed by a cover 75 which simultaneously serves as a rear stopper for the drive piston 24. Stopper means comprised of a rigid and an elastic plate 45, 46 are provided between the cover 75 and the proximal end face 44 of the drive pipe 25. The end of the receiving pipe 37 facing away from the head unit 2 is closed by a plug 76 which is formed with a connecting piece 77 for the supply of compressed air. The drive pipe 25 is provided with lateral openings 47 located adjacent to the cover 75 which communicate with the opening in the connecting piece 77 via a chamber 78 formed between the plug 76, the sealing bush 42, the receiving pipe 37 and the drive pipe 25.

Next, the operation of the above described ejection device 1 will be explained. As described with reference to FIGS. 1 and 2, the drive piston 24 is driven by compressed air to perform a periodically reciprocating movement. However, as opposed to the previously described embodiment, the drive piston 24 abuts against the intermediary member 58 and excites a compression wave therein which is transmitted to the working piston 5 by said intermediary member 58 and causes the pressure chamberfacing end of the working piston 5 to be displaced into the pressure chamber 13. As a result, liquid is ejected from the ejection opening 11 via the outlet 7 and the nozzle 9 as described above. The O-ring 21 provided around the working piston 5 to seal the pressure chamber 13 is radially pressed against the working piston 5 by the threadingly adjustable clamping ring 16 so that the working piston 5 may be displaced into the pressure chamber 13, i.e. to the left as shown in FIGS. 3 and 4, by the compression wave caused by the drive piston 24 and travelling into the direction of the impact, but cannot be displaced in the reverse direction, i.e. out of the pressure chamber 13, by the reflected compression wave which is weaker than the incident one. Further, the O-ring 65 arranged between the inwardly facing annular flange 63 of the receiving sleeve 31 and the intermediary member 58 is biased in such a way that it exerts a radial pressure on the intermediary member 58 to prevent any displacement of the intermediary member 58 relative to the O-ring 65 unless it is caused by the impact acting towards the pressure chamber 13.

Thus, the working piston 5 travels by a predetermined distance into the pressure chamber 13 upon each impact transmitted thereon by the drive piston 24, with a small amount of liquid being ejected during its motion, and is held at its new position due to the linear reverse stopping effect achieved by means of the O-rings 21, 65 until the drive piston 24 abuts again. The intermediary member 58 coupled to the working piston 5 by means of the coupling sleeve 68 moves along with the working piston 5.

When the working piston 5 has moved into the pressure chamber 13 so that it abuts against the—with reference to FIGS. 3 and 4—left end of the cavity 4, the head unit 2 may be removed and refilled, or replaced by another head unit. For this purpose, the head unit 2 may simply be unscrewed from the drive unit 23 as previously described, so that it may be cleaned, sterilized and refilled as will subsequently be explained, or replaced by a new head unit 2.

The connecting force between the coupling sleeve 68 and the working piston 5 is so weak that the working piston automatically separates from the coupling sleeve 68 when the head unit 2 is removed from the drive unit 23. Next, the clamping ring 16 may be unscrewed from the head unit body 3 so that the O-ring 21 no longer exerts a radial pressure on the working piston 5. As a result, the working piston 5 may easily be removed from the head unit body 3 together with the O-ring 21. Finally, the nozzle 9 may be removed from the head unit body 3. The separated, individual components of the head unit 2 are now easily accessible by cleaning tools and may, thus, be cleaned and sterilized without difficulty.

After the sterilizing procedure, the O-ring 21 and the working piston 5 may be reinserted into the head unit body 3. Next, the clamping ring 16 is threaded into position. The head unit 2 may now be refilled through the outlet 7, for example, after which the nozzle 9 including the cap 12 may be mounted to the head unit 2. However, the head unit 2 may also be refilled while the nozzle 9 and the cap 12 are mounted thereto, for example via the cavity 4 which has not yet been closed by the working piston 5. In both cases, the working piston 5 may be moved into the pressure chamber 13 by a certain distance after the filling procedure so that any air bubbles trapped therein are forced out through the ejection opening 11.

To assemble the two units 2, 23 of the device, the intermediary member 58 is returned to its starting position, i.e. it is moved until the annular flange 62 abuts against the end face 32. When the intermediary member 58 has reached said starting position, the end face 84 of the coupling sleeve 68 distal to the head unit abuts against the inner shoulder 85 of the receiving sleeve 31. When the head unit 2 is threaded into the drive unit 23, the working piston 5 is automatically pushed into the coupling sleeve 68 in the axial direction thereof because the coupling sleeve 68 is, in the assembling direction of the head unit 2, fixed against displacement relative to the intermediary member 58 by the abutment of its end face against the stop formed by the inner shoulder 84 of the receiving sleeve 31. Alternatively, the coupling sleeve 68 may be fixed to the intermediary member 58 in a way which prevents at least an axial relative displacement between the coupling sleeve 68 and the intermediary member 58.

To ensure a close fit between the working piston 5 and the intermediary member 58, i.e. a no-play abutment of their end faces, the arrangement of the working piston 5 prior to the assembly of the head unit 2 and the drive unit 23 is preferably such that it protrudes from the cavity 4 in the direction towards the drive unit 23 by at least such a distance that it abuts against the intermediary member before the head unit 2 is fully threaded onto the drive unit 23. This is achieved by filling the pressure chamber 13 with a suitable amount of liquid. When threading the head unit 2 onto the drive unit 23, the ejection opening 11 is first kept closed so that the working piston 5 cannot move into the pressure chamber 13 to eject liquid therefrom while being coupled with the intermediary member 58. As soon as the working piston 5 and the intermediary member 58 have been connected, which is indicated by the fact that the head unit 2 cannot be threaded any further onto the drive unit 23, the ejection opening 11 may be opened so that the head unit 2 may be threaded to its final position on the drive unit 23. During this step, any air bubbles present in the pressure chamber 13 are forced out, similar to the venting of a syringe. Afterwards, the ejection opening 11 may be closed by the cap 12.

FIGS. 5 to 7 show a filling device which may be used to refill one or several head units 2 of the ejection device 1 according to the present invention.

The filling device comprises an elongate frame 79 having a U-shaped cross section as seen perpendicularly to its longitudinal direction. One of the legs of said U-shaped frame forms a horizontal frame base 80, and the other leg forms a horizontal support member 81. The support member 81 and the frame base 80 are connected by the web 82 of the U-shaped frame 79. The support member 81 comprises threaded holes 83 which are spaced apart in the longitudinal direction of the frame 79. Each threaded hole 83 is firmly connected with a head unit 2, i.e with the annular flange 15 formed at the head unit body 3 thereof, which has been threaded into the hole. The working pistons 5 of the head units 2 threaded into the holes 83 extend vertically and may each be positioned to abut against the frame base 80 so that the volume of the cavity 4 formed in the respective head unit body 3, and thus the volume of the respective pressure chamber, is precisely adjusted. The support member 81 may be designed to be vertically adjustable so that different pressure chamber volumes may be provided. Alternatively, the distance by which the head units 2 are threaded into the support member 81 may be varied to achieve different pressure chamber volumes. For this purpose, the frame 79 is preferably provided with display or indicator means which show how far the head unit body 3 has been threaded into the frame.

To replenish the pressure chamber 13, the nozzle 9 may be removed so that the liquid may be refilled through the outlet 7 by means of a syringe, for example. Afterwards, the nozzle 9 is returned to its assembled position at the head unit, together with the cap 12. Alternatively, the liquid may be filled directly into the pressure chamber 13 before the working piston 5 is inserted into the cavity 4. To prevent air from being trapped in the pressure chamber 13, the final turns to thread the head unit 2 fully into the support member 81 may be carried out after the filling so that any air present in the pressure chamber 13 is forced out through the ejection opening 11, similar to the venting of a syringe. Afterwards, the cap 12 is placed on the nozzle 9.

FIGS. 8 and 9 show a longitudinal section of an ejection device 1 for the high-pressure ejection of liquids according to another embodiment of the present invention. The ejection device 1 corresponds to that shown in FIGS. 1 and 2, except for the lateral openings 41 which are formed as longitudinal slots in the present embodiment. The pressure chamber-facing ends 82 of the longitudinal slots define the maximum displacement range of the working piston 5 into the pressure chamber 13. That is, the working piston 5 may be displaced into the pressure chamber 13 until its end 67 facing the drive piston 24 reaches the ends 82 of the longitudinal slots. At this point, the longitudinal slots are completely covered by the drive piston 24 abutting against the working piston 5 because the length of the drive piston 24 exceeds that of the longitudinal slots, so that the compressed air in the annular chamber 40 cannot flow back into the drive pipe 25 to return the drive piston 24 to its starting position.

The principal structure of the embodiment shown in FIG. 10 of the inventive high-pressure ejection device is similar to that shown in FIG. 3 and will therefore not be described again. However, in the embodiment according to FIG. 10, the intermediary piston 58 and the working piston 5 are not coupled with each other but may be displaced independently and separately in the axial direction. Further, after the impact has been transmitted to the working piston, the intermediary piston 58 may be stepwise adjusted in accordance with the displacement of the working piston.

The intermediary piston 58 is slidingly guided in a pot-like stopper member 100 and in the drive pipe 25 which is rotatably and slidingly guided in the plug 76. The stopper member 100 is integrally and fixedly coupled with the drive pipe 25 and comprises an external thread which engages into an internal thread 101 formed in the receiving pipe 37, whereby a screw-type adjustment of the stopper member is enabled. In the annular chamber 40, a pressure spring 103 is arranged to be biased between the plug 76 and the stopper member 100 so that the stopper member 100 is supported at the thread 101 without play. The drive pipe 25 protrudes axially from the casing and comprises an adjusting wheel 104 by means of which the drive pipe, and thus the stopper member 100, may be rotatably adjusted.

The intermediary piston 58 comprises a radially outwardly protruding flange 105 which engages between the free front face of the drive pipe 25 and the bottom surface of the stopper member 100. An elastic buffer 102 in the form of a damping ring is arranged between the flange 105 and the bottom surface of the stopper member 100. The intermediary piston 58 is slidingly received in both the drive pipe 25 and the bottom surface of the stopper member 100 so that it may be displaced towards the working piston 5 and against the spring force of the annular buffer 102 by a predetermined distance when it is impacted by the drive piston 24. As a result, a dampened elastic impact is transmitted to the working piston 5, wherein the degree of dampening may be defined by adjusting the position of the stopper member 100 and of the intermediary member.

The coupling plate between the end of the drive pipe 25 and the threaded surface of the stopper member 100 is provided with venting holes 106 so that the space between the intermediary piston and the inner surface of the pot-shaped stopper member 100 is relieved from pressure.

Subsequently, the operation of the ejection device according to FIG. 10 will be described, starting at a state when the working piston 5 has already performed a displacement stroke. The volume of the subsequent ejection shot is adjusted by accordingly turning the adjusting wheel 104. For example, a volume of 1.5 μl for each 15°-turn of the adjusting wheel 104 corresponds to a pitch of the thread 101 of 14×1. The turning motion is transmitted from the adjusting wheel 104 to the stopper member 100 via the drive pipe 25 so that the stopper member 100 is threadingly displaced within the thread 101 of the receiving pipe 37 by a corresponding axial distance in the direction towards the working piston 5. Thereby, the pressure spring 103 presses the stopper member 100 without play against the thread 101 and towards the working piston. The drive pipe 25 is carried along to be displaced by the same axial distance, and acts upon the flange of the intermediary piston 58 to cause the displacement thereof by the same amount.

Next, the drive piston 24 is accelerated by pulses of compressed air supplied through the lateral connecting piece 77 until it strikes on the intermediary piston 58, with the displaced air being vented into the annular chamber 40 through the lateral openings 41 in the drive pipe 25. The venting holes 106 provide for a compensation of the pressure which builds up behind the flange 105 of the intermediary piston 58 so that the latter is not pressurized before it is hit by the drive piston. When the drive piston 24 strikes on the intermediary piston 58, the intermediary piston 58 receives an impact pulse so that it moves at a higher speed than the drive piston 24, which is due to its lower mass, and transmits the impact pulse to the working piston 5 until the intermediary piston abuts against the stopper member 100. As shown in the embodiment according to FIG. 10, this abutment may be dampened by an elastic buffer 102 or any other suitable dampening means. However, the buffer 102 or otherwise embodied dampening means may also be dispensed with so that the intermediary piston 58 abuts unbufferedly against the stopper member 100.

The stopper member 100 and/or the intermediary member 58 may be adjusted manually, or automatically by means of a stepper drive which is manually actuated or controlled in accordance with the ejection sequence, i.e. with the drive cycle of the drive piston. It is also possible to provide a fully automatically controlled stepper drive which responds to a discrete state, which may be the pressure increase in the annular chamber, the impact of the drive piston on the intermediary member or the impact of the intermediary member on the working piston, or the return of the drive piston to its initial position, for example.

What is claimed is:

1. An ejection device (1) for the high-pressure ejection of a liquid or a liquid containing solid particles, comprising a pressure chamber (13) wherein the liquid is received, which opens into an ejection opening (11) and is delimited by a working piston (5) which, upon application of an impact on its end facing away from the pressure chamber, is capable of transmitting a compression wave by which at least the pressure chamber-facing end of the working piston (5) is displaceable by a predetermined displacement stroke into the pressure chamber (13) so that the volume thereof is reduced, with the reduction in volume of the pressure chamber (13) being significantly smaller than the volume of the pressure chamber (13); and a drive member (24) which is capable of generating the impact, characterized in that the working piston (5) is progressively displaced into the pressure chamber (13) by the repeated application of impacts, with the distance of each single displacement being defined by the predetermined displacement stroke.

2. An ejection device (1) according to claim 1, characterized in that the working piston (5) is supported by linear reverse stopping means so that any reverse displacement thereof is prevented.

3. An ejection device (1) according to claim 1 or 2, characterized in that the working piston (5) is provided with two elastic sealing elements (18, 21) is arranged at a distance from each other to seal the, circumference of the working piston (5) against an associated wall member, and that said distance between the two sealing elements (18, 21) is greater than the total working stroke of the working piston (5), wherein a gas-filled annular chamber (22) surrounding the working piston (5) is formed between the two sealing elements (18, 21).

4. An ejection device (1) according to any one of the claims 1 to 3, characterized in that an intermediary member (58) is provided as a separate component between the working piston (5) and the drive member (24), which transmits the elastic impact from the drive member (24) to the working piston (5).

5. An ejection device (1) according to claim 4, characterized in that the working piston (5) and the intermediary member (56) are separably connected to each other by means of a coupling (68).

6. An ejection device (1) according to any one of the claims 4 to 5, characterized in that the linear reverse stopping means are provided at the working piston (5) and/or at the intermediary member (56).

7. An ejection device (1) according to any one of the claims 4 to 6, characterized in that the linear reverse stopping means are formed by at least one elastic sealing element (18, 21; 65) which seals the circumference of the working piston (5) or of the intermediary member (58) against their associated wall member.

8. An ejection device (1) according to any one of the claims 4 to 7, characterized in that the linear reverse stopping means are formed by at least two elastic sealing elements (18, 21; 65), each of which seal the circumference of one of the working piston (5) and the intermediary member (58) against their associated wall member.

9. An ejection device (1) according to claim 7 or 8, characterized in that the linear reverse stopping means comprise an O-ring (18, 21) as a sealing element which is axially compresseable by an adjustable clamping ring (16) so that a radial pressure is exerted on the working piston (5) and the intermediary member (58) respectively.

10. An ejection device (1) according to claim 9, characterized in that the linear reverse stopping means comprise another O-ring (21) which is axially spaced apart from the first O-ring (18) by a distance sleeve (10) arranged adjacent to the adjustable clamping ring (16), and which may be axially compressed by means of the adjustable clamping ring (16), with the distance sleeve (19) acting as a power transmitting member, so that a radial pressure is exerted on the working piston (5) and the intermediary member (58), respectively.

11. An ejection device (1) according to any one of the claims 1 to 10, characterized by a head unit (2) wherein the working piston (5) and at least a portion of the pressure chamber (13) are provided, and a drive unit (23) wherein the drive member (24) and the intermediary member (58), respectively, are provided, with the head unit (2) and the drive unit (23) being formed as independent, separate units of the ejection device which are connected to each other by means of a separable coupling.

12. An ejection device (1) according to claim 11, characterized in that at least a portion of the pressure chamber (13) is formed by a cavity (4) provided in the head unit (2) and accommodating the working piston (5) as well, with the bottom of the cavity (4) being shaped such that it conforms with the opposing end face (51) of the working piston (5).

13. An ejection device (1) according to any one of the claims 11 to 12, characterized in that the head unit (2) is designed as an exchangeable disposable unit.

14. An ejection device (1) according to any one of the claims 11 to 12, characterized in that the head unit (2) is designed as a refillable unit which is removable from the drive unit (23) to be refilled.

15. An ejection device (1) according to any one of the claims 1 to 14, characterized in that the drive member (24) is designed as a pneumatically driveable drive piston (24) which is arranged in a drive pipe (25) that comprises a longitudinal slot at its end portion facing towards the working piston (5), said longitudinal slot providing a fluid communication between the interior of the drive pipe (25) and a venting chamber (40), the drive piston (24) is returnable to its starting position by means of the pressure generated by the air forced through the longitudinal slot into the venting chamber (40) and compressed therein, until the drive piston (24) reaches the working piston-facing end of the longitudinal slot.

16. An ejection device (1) according to any one of the claims 1 to 15, characterized by an endoscopic catheter comprising a liquid-carrying passage which forms a portion of the pressure chamber (13).

17. An ejection device (1) according to claim 5, characterized in that the intermediary member (58) transmitting the impact from the drive member (24) to the working piston (5) may be axially adjusted towards the working piston (5) after the impact has been transmitted.

18. An ejection device (1) according to claim 17, characterized in that the intermediary member (58) is displaceable towards the working piston (5) by the drive member (24), until it abuts against a stopper member (100) which is axially adjustable towards the working piston (5).

19. An ejection device (1) according to claim 18, characterized in that a buffer (102) is at arranged between the stopper member (100) and the intermediary member (58), which serves to elastically dampen the impact of the intermediary member.

20. An ejection device (1) according to claim 18 or 19, characterized in that the stopper member (100) is axially adjustable by means of a thread (101), and supported by a spring (103) so that it abuts at said thread without play.

21. An ejection device (1) according to any one of the claims 19 to 20, characterized in that the stopper member (100) and the intermediary member (58) are adjustable by means of a drive pipe (25) wherein the drive member (24) is arranged and which is displaceably guided.

22. An ejection device (1) according to any one of the claims 18 to 21, characterized in that a stepper drive is provided for adjusting the stopper member (100).

* * * * *